(12) United States Patent
Nagai et al.

(10) Patent No.: US 6,855,803 B2
(45) Date of Patent: Feb. 15, 2005

(54) PROTEIN HAVING HEMOLYTIC ACTIVITY AND GENE ENCODING THE PROTEIN

(75) Inventors: Hiroshi Nagai, Tokyo (JP); Terumi Nakajima, Tokyo (JP); Kyoko Kuroda, Kyoto (JP)

(73) Assignee: Suntory Limited, Osaka (JP)

( * ) Notice: Subject to any disclaimer, the term of this patent is extended or adjusted under 35 U.S.C. 154(b) by 275 days.

(21) Appl. No.: 09/979,275

(22) PCT Filed: Mar. 21, 2001

(86) PCT No.: PCT/JP01/02209

§ 371 (c)(1),
(2), (4) Date: Nov. 21, 2001

(87) PCT Pub. No.: WO01/70799

PCT Pub. Date: Sep. 27, 2001

(65) Prior Publication Data

US 2004/0110919 A1 Jun. 10, 2004

(30) Foreign Application Priority Data

Mar. 21, 2000 (JP) ........................................ 2000-078967

(51) Int. Cl.$^7$ ........................... C07K 14/00; C07K 1/00

(52) U.S. Cl. ....................... 530/300; 530/350; 435/69.1

(58) Field of Search ................................. 530/300, 350; 435/69.1

(56) References Cited

U.S. PATENT DOCUMENTS 6,653,449 B1 * 11/2003 Nagai et al. ................. 530/350

FOREIGN PATENT DOCUMENTS

WO 9950294 10/1999

OTHER PUBLICATIONS

Nagai H. et al. "Isolation and characterization of a novel protein toxin from the Hawaiian box jellyfish (sea wasp) *Carybdea alata*." Biochem Biophys Res Commun. Aug. 28, 2000; 275(2):589–594.*
Rottini, et al. "Purification and properties of a cytolytic toxin in venom of the jellyfish *Carybdea marsupialis*" Toxicon, 1995, 33, 3, pp. 315–326.

* cited by examiner

*Primary Examiner*—Karen Cochrane Carlson
*Assistant Examiner*—Anand Desai
(74) *Attorney, Agent, or Firm*—Crowell & Moring LLP

(57) ABSTRACT

Novel proteins having hemolytic activity giving the new approach of development of the drugs, and having the following property are provided:
  (1) having hemolytic activity;
  (2) having a molecular weight of about 50,000 Da (determined by SDS gel electrophoresis); and
  (3) having an amino acid sequence represented by any of SEQ ID NO 1 and SEQ ID NO 2 as a partial amino acid sequence represented by the following amino acid sequences (1) and (2);
Amino acid sequence (1):
Tyr-Arg-Asp-Gln-Glu-Leu-Glu-Asp-Asn-Val-Lys
Amino acid sequence (2):
Lys-Trp-Pro-Asp-Tyr-Phe-Val-Tyr-Met-Glu-Ser-Ser-Ala-His-Gly-Tyr-Ile-Arg
(wherein, an amino acid residue is written by the 3 letters notation defined by IUPAC and IUB)
obtained from nematocyst of *Carybdea alata*.

9 Claims, No Drawings

SEQUENCE LISTING

<160> NUMBER OF SEQ ID NOS: 12

<210> SEQ ID NO 1
<211> LENGTH: 11
<212> TYPE: PRT
<213> ORGANISM: Carybdea alata

<400> SEQUENCE: 1

Tyr Arg Asp Gln Glu Leu Glu Asp Asn Val Lys
 1               5                  10

<210> SEQ ID NO 2
<211> LENGTH: 18
<212> TYPE: PRT
<213> ORGANISM: Carybdea alata

<400> SEQUENCE: 2

Lys Trp Pro Asp Tyr Phe Val Tyr Met Glu Ser Ser Ala His Gly Tyr
 1               5                  10                  15

Ile Arg

<210> SEQ ID NO 3
<211> LENGTH: 463
<212> TYPE: PRT
<213> ORGANISM: Carybdea alata

<400> SEQUENCE: 3

-continued

```
Met Ser Arg Gly Tyr Ser Leu His Leu Val Leu Phe Val Leu Ser
 1               5                  10                  15

Thr Ala Phe Pro Ser Gln Ala Arg Leu Ser Arg Tyr Arg Arg Ser Ala
            20                  25                  30

Ala Asp Ala Val Ser Thr Asp Ile Asp Gly Ile Ile Gly Gln Leu Asn
        35                  40                  45

Asp Leu Gly Thr Asp Thr Lys Arg Leu Lys Glu Ala Leu Gln Gly Val
    50                  55                  60

Gln Glu Ala Val Lys Lys Glu Pro Ala Thr Thr Ile Ala Lys Val Ser
65                  70                  75                  80

Thr Ile Val Gly Ser Val Gly Gly Ser Leu Ser Lys Phe Lys Ser Gly
                85                  90                  95

Asp Pro Phe Asp Val Ala Ser Gly Cys Leu Asp Ile Ile Ala Ser Val
                100                 105                 110

Ala Thr Thr Phe Gly Gly Pro Tyr Gly Ile Ala Ile Gly Ala Val Ala
            115                 120                 125

Ser Leu Ile Ser Ser Ile Leu Ser Leu Phe Ser Gly Asn Ser Met Gly
    130                 135                 140

Ser Ala Ile Lys Gln Val Ile Asp Asp Ala Phe Lys Lys Tyr Arg Asp
145                 150                 155                 160

Gln Glu Leu Glu Asp Asn Val Lys Gly Ala Lys Arg Thr Phe Asn Ala
                165                 170                 175

Val Ile Thr Phe Val Asn Ser Val Ser Lys Thr Glu Asn Leu Thr Glu
            180                 185                 190

Val His Leu Asp Ser Val Arg Asp Ala Val Arg Val Asp Ala Phe Thr
    195                 200                 205

Asn Met Leu Gly Val Leu Glu Ser Arg Ile Asn Arg Gly Ser Val Ser
210                 215                 220

Thr Asp Asn Asn Glu Ala Met Arg Thr Ile Asn Phe Ile Phe Leu Tyr
225                 230                 235                 240

Leu Gln Leu Ser Val Met Arg Glu Thr Leu Leu Thr Gln Val Ile Leu
                245                 250                 255

Leu Tyr Lys Arg Ala Gly Gly Ala Tyr Asp Glu Leu Ala Leu Ser Leu
            260                 265                 270

Ser Leu Thr Ser Asp Gln Asn Lys Glu Ala Thr Arg Glu Thr Val Thr
    275                 280                 285

Phe Leu His Gln Met Glu Thr Lys Tyr Ser Leu Cys Gly Ser Tyr Tyr
290                 295                 300

Tyr Pro Ile Asp His Ser Lys Ala Ala Ile Gly Ile Leu Lys Leu Thr
305                 310                 315                 320

Lys Phe Phe Gly Val Pro Asp Pro Ala Arg Tyr Thr Phe Asp Gly Leu
                325                 330                 335

Tyr Tyr Arg Met Gln Asn Arg Ala Trp Asn Arg Tyr Ser Ile Cys Lys
            340                 345                 350

Glu Ser Tyr Ala Gly Asn His Met Phe Arg Gly Cys Lys Asp Ser Ser
    355                 360                 365

Tyr His Gly Ile Arg Ile Lys Lys Leu Glu Asn Gly Tyr His Thr Ile
370                 375                 380

Thr Leu Arg Ser Lys Ala Met Tyr Val Thr Lys His Ala Gln Gly Trp
385                 390                 395                 400

Gly Trp Gly Thr Ala Asp Glu Asp Pro Gly Glu Gln Gly Tyr Phe Thr
                405                 410                 415
```

```
Phe Ile Pro Leu Thr Asn Gly Phe Tyr Met Val Ser Thr Lys Lys Trp
                420                 425                 430

Pro Asp Tyr Phe Val Tyr Met Glu Ser Ser Ala His Gly Tyr Ile Arg
            435                 440                 445

Ser Trp His Tyr Asn Pro Asp Pro Gln Gly Gln Trp Lys Ile Leu
    450                 455                 460

<210> SEQ ID NO 4
<211> LENGTH: 2042
<212> TYPE: DNA
<213> ORGANISM: Carybdea alata

<400> SEQUENCE: 4
taaatggacc gtgtacaggc tcatctataa aaactattat ttgtgttttt aatttcaatt     60
actagattca tcatgtctcg tggatatagc ttgcaccttg tgcttttct agttctttcc     120
acagcattcc catctcaagc tagattatcg agatatcgtc gaagcgcagc cgatgccgta    180
agcaccgata tcgacggcat cattggacag ctcaatgatc tcggtacaga taccaagcga    240
ttaaaggaag ctctacaggg agttcaggaa gctgttaaaa agagcccgc taccactatt     300
gctaaagtat caactatcgt cgggtcagtt ggaggttcat tgagcaagtt caagtcagga    360
gatccctttg atgttgcttc agggtgtctg acatcattg ccagtgttgc tacaacattt     420
ggaggtccat acgggattgc tattggggca gtagcatcat tgatttcctc tattcttagc    480
ctcttctctg aaatagtat gggaagtgca atcaaacaag ttattgacga cgctttcaag     540
aaatatcgcg atcaagagtt ggaagacaat gtaaaggag caaaaggac ctttaatgcc      600
gtcatcacct tcgtcaacag tgtatcaaag acagagaatc tgaccgaggt ccatttggat    660
tcggtcagag atgctgttag agttgatgca tttaccaaca tgctaggtgt cttggagagc    720
agaatcaatc gcggctctgt gtccaccgat aacaatgaag caatgagaac catcaatttc    780
atcttcttgt acttacaact gtccgtgatg cgtgaaacac tgttgactca agttattctt    840
ttgtacaagc gtgcgggtgg tgcatatgat gagctggcac tgtctctgtc cttaacaagt    900
gatcaaaaca aggaagcgac aagagaaacg gttacgtttt tacatcaaat ggaaaccaag    960
tattctctct gtggttccta ctactaccct attgaccact ctaaggcagc cattggtatt   1020
cttaaactca caaatttttt tggagtgcca gatcctgcaa gatacacgtt tgatggtctt   1080
tattacagaa tgcaaaacag ggcatggaat cggtatagca tctgtaaaga atcttatgcg   1140
ggcaatcaca tgtttcgggg ctgcaaagat tcaagttacc atggaattag gatcaaaaag   1200
ctggaaaatg gttaccatac tattaccctg agatcaaaag ccatgtatgt cacgaaacac   1260
gctcaaggat ggggctgggg aacagctgat gaagatccag gtgagcaagg ttacttcact   1320
ttcatcccct taacaaatgg ttttttacatg gtttctacca agaagtggcc agattacttt   1380
gtgtacatgg aaagcagtgc gcatggttat attcgaagct ggcattacaa ccctgatcca   1440
cagggacaat ggaaaatctt gtaattgcta cggtgatttt tgaagttatc ccagataatg   1500
actcagtcat agagcaatcg ttagagttgc ttcataatct aagttgcatt tctcgaacac   1560
gcatgcgtcg gagttgctaa tacgtcctac gaacaggtgt attctgattt agtcctggtg   1620
atttctttac ttgtattttt acgctattct caaagagttt caattttcga cgcagagact   1680
aaatgtagat taaacgattt ttgtggtgtc aaagaaaagg aaaggaacag tgttgctttg   1740
tagtaccacg gaaataaaag tgaaagacca ctcaatgcat tgttttcatg ctgaaaatag   1800
aagtagtcac aactaacaaa cttcaattct aatatttcaa ttgtttattc atttgctctc   1860
```

```
ttttcccttc caacaaccgc tgcaagtgat caatttatct acaagttagt aatcattaac    1920
actatcgttg atcgtcctcg gataactcga atataattca tgcgtccagc gagtttgact    1980
tatgtatctt agattgtgta gcatatcagc atatcaataa aatatcacaa aaaaaaaaa     2040 aa                                                                   2042
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (12)
<223> OTHER INFORMATION: i

<400> SEQUENCE: 5

```
gaycargary tngargayaa                                                  20
```

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i

<400> SEQUENCE: 6

```
atrtanccrt gngcnswnsw ytcc                                             24
```

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: this sequence may encompass 12-18 nucleotides

<400> SEQUENCE: 7

```
tttttttttt tttttttt                                                    18
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8

```
acagcatctc tgaccgaatc                                                  20
```

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
aatggacctc ggtcagattc                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
cactgttgac gaaggtgatg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
ggaacagctg atgaagatcc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
ggtgagcaag gttacttcac                                              20
```

PROTEIN HAVING HEMOLYTIC ACTIVITY AND GENE ENCODING THE PROTEIN

This application is a National stage of PCT/JP01/02209 filed Mar. 21, 2001

TECHNICAL FIELD

The present invention relates to novel proteins having a hemolytic activity and genes encoding thereof. More specifically, the present invention relates to novel proteins having the hemolytic activity, a process for producing thereof, reagents, pesticides and medicines utilizing physiological activities thereof.

BACKGROUND ART

The sting injury by the jellyfish in sea bathing has occurred in various parts of the world. The sting injury by *Carybdea rastonii* or *Physalia physalis* has also occurred frequently in Japan every year in the season of sea bathing of the summertime. The degree of the symptom by sting differs by species of a jellyfish and the individual differences of patients. The first symptom is dermotoses, such as pain, flare, papule, vesicle and so on in the sting site. In a serious illness, patients may die with generating of hemorrhagic maculae and the necrosis, and also constitutional symptom, such as headache, high fever, nausea, dyspnea, and the fluctuation of a pulse. Although such sting injury is occurring frequently, the determination and pharmacological properties of the toxic components of jellyfish have not been studied intensively. Therefore, the development of medicines for treatment of the sting by the jellyfish is hardly performed before the present invention.

For example, the serious sting injury by *Carybdea alata* in Hawaii or other places has been reported (R. H. Tamanaha et al., J. Am. Acad. Dermatol., 1996, 35, 991–993); however, the determination and pharmacological properties of the toxic components of this jellyfish have not been studied. On the contrary, the studies on the toxic components of *Carybdea rastonii*, which is family relation to *Carybdea alata*, have been well studied, and chemical and physiological properties of the toxic component of *Carybdea rastonii* have been clarified (Akihiko Sato, "Research on the toxic component of *Carybdea rastonii*", The Journal of the Ochanomizu Medico-dental Society, vol. 33, No. 2, 131–151, June, 1985; International Laid-open Patent Publication No. WO99/50294).

On the one hand, since the known poisons from the nematocyst of a jellyfish were non-dialyzable high polymer and deactivated by treatment with acid or alkali, or by heating processing, organic solvent processing, protease processing, etc., it was thought that the main components of poison were proteins.

Moreover, the purification of the protein toxin derived from a jellyfish has also been tried; however, the isolation and the purification of the active components maintaining the hemolytic activity were not performed since the toxin of a jellyfish itself was very easy to be deactivated. Therefore, the physical and chemical properties of the toxin from jellyfish have never been clarified up to now. However, the method for isolation and purification of the unstable toxic components of jellyfish in good yields has been reported recently in the International Laid-open Patent Publication No. WO99/50294.

The detailed studies on the toxic component of a jellyfish is very important for the development of drugs applying their various physiological activities, in particular, specific hemolytic activity and the cytotoxic effect, and for the development of medicines for treatment of the sting injury by the jellyfish.

Therefore, the problems to be solved by the present invention is providing an approach to development of the drugs for treatment of the sting injury by the jellyfish by means of isolating the proteins or peptides having as potent hemolytic activity as possible, in the state where the physiologic activity is retained. The present invention further provides the approach to study similarities on embryology or structure, and the species specificity of the protein having hemolytic activity to evaluate the structure-activity relationship thereof.

DISCLOSURE OF THE INVENTION

The inventors extensively performed the research for isolating the proteins having the hemolytic activity from the nematocyst of *Carybdea alata* using the hemolytic activity as the parameter, while retaining these hemolytic activities. As the result, they found out the process for isolating and purifying the proteins retaining hemolytic activities, and clarified the protein from *Carybdea alata* having the partial chemical structure consisting the following amino acid sequences (1) and (2), and the molecular weight of about 50,000 Da (determined by SDS gel electrophoresis).

Amino Acid Sequence (1):

Tyr-Arg-Asp-Gln-Glu-Leu-Glu-Asp-Asn-Val-Lys

Amino Acid Sequence (2):

Lys-Trp-Pro-Asp-Tyr-Phe-Val-Tyr-Met-Glu-Ser-Ser-Ala-His-Gly-Tyr-Ile-Arg (wherein, an amino acid residue is written by the 3 letters notation defined by IUPAC and IUB)

Furthermore, they prepared the primers based on their partial chemical structures of the protein, and analyzed the gene sequence of about 900 base pair of said protein by conducting the RT-PCR to total RNA prepared from the tentacle of *Carybdea alata* by using these primers. Consequently, they further determined the full primary amino acid sequence of the hemolytic active protein of *Carybdea alata* by means of analyzing the gene sequence in 5'-end and 3'-end using the 5' RACE method and 3' RACE method.

Therefore, one embodiment of the present invention provides the specific protein having the amino acid sequence represented by SEQ ID NO 3, or the amino acid sequence modified by the addition and deletion of one or more amino acid, and/or the substitution by other amino acid to said amino acid sequence, with the above-mentioned physiological, physical and chemical properties.

Another embodiment of the present invention also provides the process for preparing such proteins.

Furthermore, another embodiment provides the gene encoding such proteins, the process for preparing the specific proteins using the gene, and the drugs or the pesticides using the same.

The present invention further provides the pharmaceutical compositions containing the proteins using these properties, particularly, the pharmaceutical compositions having the platelet agglutination effect etc., or the pesticides utilizing the cytotoxic properties of the proteins.

Moreover, since a specific antibody can also be obtained from this hemolytic active protein according to a conventional method (Cell Technology, separate volume, "*Experimental protocol of antipeptide antibody*", Shujunsha Co.), the present invention also provides the pharmaceutical compositions containing said antibody.

BEST MODE FOR CARRYING OUT THE INVENTION

The isolation and purification of the proteins having the specific physiological activity provided by the present invention can specifically be performed as follows. For example, the ultrasonication of the nematocyst of *Carybdea alata* is carried out in phosphoric acid buffer solution, and then supernatants are collected by the centrifugal separation to obtain a crude extract. The object proteins can be separated and purified by subjecting this crude extract to ion exchange high performance liquid chromatography using an ion exchange column such as TSK-GEL (Toso Co.), and the gel filtration high performance liquid chromatography with a gel filtrate column such as Superdex-75 (Pharmacia Co.).

The structure of the protein provided according to the present invention obtained in this way can be determined by combining the analysis procedure of the amino acid sequence by the selective degradation using the enzyme, and the analysis procedure of a gene sequence using the PCR method or the like. For example, the amino acid sequence can be determined by processing the protein separated and purified as mentioned above with a lysyl- endopeptidase, fractionating the fragment using a high performance liquid chromatography, and analyzing it using an amino acid sequencer or the like. Next, the gene sequence of the proteins can be determined by RT-PCR method or the like using the primers prepared on the basis of the amino acid sequence. Finally, the full primary amino acid sequence of the proteins can be clarified by determining the amino acid sequence on the basis of the gene sequence.

It was confirmed by such analysis that the protein provided according to the present invention has the molecular weight of about 50,000 Da (measured by SDS gel electrophoresis), and the partial amino acid sequences have the above-mentioned amino acid sequences (1) and (2).

As a result of a homology search on the partial amino acid sequences, except for exhibiting about 40% of homology between the protein of the present invention and the hemolytic active proteins from *Carybdea rastonii*, which is family relation to *Carybdea alata*, the homology between the protein of the present invention and the known other proteins was very low. Therefore, it was suggested that the protein of the present invention having the hemolytic activity is completely novel protein, which is not similar to the known proteins.

Next, the determination of the gene sequence of about 1.000 base pairs by performing RT-PCR to total RNA prepared from the tentacle of *Carybdea alata* using the primers prepared on the basis of the partial amino acid sequence, and the determination of the gene sequences of the 5'-end and the 3'-end using the 5' RACE method and 3' RACE method were performed. Consequently, it is concluded that the hemolytic active protein of *Carybdea alata* has the full primary amino acid sequence represented by SEQ ID NO 3, and the gene encoding thereof has the base sequence represented by SEQ ID NO 4.

The method for preparing the specific protein of the present invention by separation and purification is characterized in retaining the hemolytic activity. For example, the separation and the purification in the state of retaining such hemolytic activity are attained by performing the processing such as ultrasonication using the above-mentioned phosphoric acid buffer solution or various high performance liquid chromatography in 10 mM phosphoric acid buffer solution (pH 6.0) containing above 0.1 M NaCl, preferably above 0.3 M, and more preferably above 0.5 M, at below 10° C., preferably below 5° C.

Therefore, the present invention also provides the method for preparing the protein by extracting and purifying them from the nematocyst of the *Carybdea alata* in the state of retaining the physiological activity.

The specific protein of the present invention also can be prepared by the gene recombination method. Preparation by the gene recombination method can be performed according to a conventional method. For example, it can be obtained by preparing the vector integrated with the gene represented by SEQ ID NO 4, transforming a host cell by the vector, incubating or growing the host cell, and isolating and purifying the proteins having hemolytic activity of interest from the host cell or culture solution.

Since the protein provided according to the present invention has hemolytic activity, for example, it may be used for the medicaments having the cytolysis effect and for the reagents for research on a hemolysis. Furthermore, it provides the new approach for the development of drugs, such as a drug for treating the sting by the jellyfish, and development of pesticides, such as an insecticide, using the hemolytic or cytotoxic activity.

EXAMPLES

The present invention will be described in detail with reference to the following examples; however, the present invention is not limited to the examples.

Example 1

1) Extraction of the Nematocyst of *Carybdea alata*

200 mg of the nematocyst of the *Carybdea alata* obtained on the Waikiki Beach, Hi. and cryopreserved at −80° C. was immersed in 8 ml of 10 mM phosphoric acid buffer solution (pH 6.0), and treated for 15 minutes by the ultrasonic wave (ultrasonic cleaner VS150, Iuchi Co.). The supernatant fluids were collected by centrifugal separation (3,000 rpm, for 20 minutes). This operation was performed 3 times in total. Furthermore, the same extraction operation was repeated 3 times with 8 ml of 10 mM phosphoric acid buffer solutions (pH 6.0) containing 1 M NaCl, and then all the supernatant fluids were collected. After the extraction operation, ion exchange HPLC (high performance liquid chromatography) of the following purification step was immediately performed.

2) The Purification by Ion Exchange HPLC (Column: TSK-GEL CM650S, Column Size: 20×220 mm, Toso Co.)

The above-mentioned column was equilibrated with 10 mM phosphoric acid buffer solution (pH 6.0) containing 0.3 M NaCl. After the equilibration, the supernatant fluids obtained by extraction in the operation of the above-mentioned 1) were combined and diluted with 10 mM phosphoric acid buffer solution (pH 6.0) to 4 times. The solution was loaded onto the above-mentioned column at a flow rate of the 3 ml/min. The column was washed with 100 ml of 10 mM phosphoric acid buffer solutions (pH 6.0) after the sample application. The elution was carried out by the 60 minutes gradient in 0 to 0.7 M NaCl concentration (in 10 mM phosphoric acid buffer solution: pH 6.0). Hemolytic activity was showed in many fractions eluting between 45 and 65 minutes after start of the gradient. In addition, hemolytic activity was examined about the hemolytic effect to sheep hemocytes (see the after-mentioned example 2).

3) The Purification by Ion Exchange HPLC (Column: TSK-GEL CM5PW, column size: 7.5×75 mm, Toso Co.)

The above-mentioned column was well equilibrated with 10 mM phosphoric acid buffer solution (pH 6.0) containing 0.3 M NaCl. The hemolytic active fractions obtained by purifying operation of the above-mentioned 2) were diluted with 10 mM phosphoric acid buffer solution (pH 6.0) to 4 times. The solution was loaded onto the above-mentioned column at the flow rate of 2 ml/min. The column was washed with 30 ml of 10 mM phosphoric acid buffer solutions (pH 6.0) after the sample application. After washing, the elution was performed by the 60 min gradient in 0 to 0.8 M NaCl concentration (in 10 mM phosphoric acid buffer solution: pH 6.0). Fractions having hemolytic activity were eluted between 25 and 35 minutes after start of the gradient, and each fraction was applied to SDS-PAGE. The separating condition of the active component was verified, and the portions separated well were collected and used in the next step. On the contrary, the portions not separated were further purified by chromatography to complete the separation of the active component.

4) Concentration of the Hemolytic Active Component by Ion Exchange HPLC (Column: TSK-GEL CM5PW, Column size: 7.5×75 mm, Toso Co.)

The column was well equilibrated with 10 mM phosphoric acid buffer solution (pH 6.0) containing 0.3 M NaCl. The hemolytic active fractions obtained by purifying operation of above-mentioned 3) were diluted with 10 mM phosphoric acid buffer solution (pH 6.0) to 4 times. The solution was loaded onto the above-mentioned column at the flow rate of 2 ml/min. The column was washed with 30 ml of 10 mM phosphoric acid buffer solutions (pH 6.0) after the sample application. After washing, 10 mM phosphoric acid buffer solution (pH 6.0) containing 0.8 M NaCl was then rinsed and the sample adhered into the column was allowed to elute. In about 5 minutes after exchange of the solvent, the portion of the hemolytic active component condensed and eluted at a stretch was collected.

5) The Purification by Gel Filtration HPLC (Column: Superdex-75, Column size: 16×600 mm, Pharmacia Co.)

Every 0.5–1.0 ml of the sample condensed by ion exchange HPLC of above 4) was applied to the above-mentioned column equilibrated with 10 mM phosphoric acid buffer solution (pH 6.0) containing 0.8 M NaCl, and allowed to elute at the flow rate of 1 ml/min. Potent hemolytic activity was found out in the fraction eluting between 50 and 60 minutes after injection of the sample. After confirming the separating condition by SDS PAGE, the protein of the present invention, a hemolytic toxin, was separated by collecting the active fractions (about 10 R9).

Example 2

Measurement of the Hemolytic Activity

Measurement of the hemolytic activity in each purification step in the above-mentioned Example 1 and measurement of the hemolytic activity of the protein of the present invention finally obtained were performed as follows.

1) Method

Hemolytic activity was measured by hemolysis to a sheep erythrocyte. That is, every 200 R1 of PBS(+) buffer solution containing 0.8% of sheep erythrocyte was put into the microwell plates of 96 wells (round bottom type). 10 µl of the solution dissolved the fraction obtained in each purification step of the above-mentioned Example 1 in 10 mM phosphoric acid buffer solution (pH 6.0) was added to the plate. It was allowed to stand at room temperature for 3 hours, and the hemolytic condition of the sheep erythrocyte of each plate was observed. In addition, the presence or absence of the retention of the hemolytic activity was determined by whether the fraction obtained in each purification step exhibits a perfect hemolysis.

2) Results 2-1) The fraction obtained in each purification step of the above-mentioned Example 1 exhibited the perfect hemolysis to the sheep erythrocyte, and therefore, it became clear that it retains the hemolytic activity.

2-2) Moreover, the protein of the present invention having the hemolytic activity finally obtained by purification operation of the above-mentioned 5) in Example 1 caused the perfect hemolysis to the sheep erythrocyte in the concentration below 100 ng/ml (about 2 nM).

Example 3

Determination of the Molecular Weight and the Partial Structure on the Proteins 3-1) Determination of the Molecular Weight The single band visualized by applying the protein of the present invention having the hemolytic activity obtained by purification operation of 5) in Example 1 to SDS gel electrophoresis (SDS-PAGE) according to the conventional method was compared with the protein molecular-weight marker (Pharmacia Co.). As the result, it was identified that the molecular weight of the protein of the present invention are about 50,000 Da.

3-2) Decomposition with the Lysylendopeptidase

The protein was decomposed by adding 3 pM of *Achromobacter* Protease I (derived from *Achromobacter lyticus* M497-1: Takara Shuzo Co.) to 10 µg of protein according to the present invention having the hemolytic activity obtained by purification operation of the above-mentioned 5) in Example 1, and incubating in 10 mM of Tris-HCl buffer solution (pH 9.0) at 30° C. for 20 hours. The protein digested with the enzyme was applied to the high performance liquid chromatography (column: Bakerbond wide pore ODS), and separated with the 60 min gradient in 10 to 62% of acetonitrile concentration (in water containing 0.1% of trifluoroacetic acid) at the flow rate of 0.7 ml/min. Consequently, two peptide fragments eluting respectively at a retention time 25 and 49 minutes were obtained.

3-3) Determination of the Amino Acid Sequence of Each Fragments by the Amino Acid Sequencer The amino acid sequence of three peptide fragments obtained as mentioned above was determined according to the conventional method using Shimadzu PSQ-1 protein sequencer (Shimadzu Co.).

As the result, two fragments have the following amino acid sequences (1) and (2), respectively:

Amino acid sequence (1):

Tyr-Arg-Asp-Gln-Glu-Leu-Glu-Asp-Asn-Val-Lys

Amino acid sequence (2):

Lys-Trp-Pro-Asp-Tyr-Phe-Val-Tyr-Met-Glu-Ser-Ser-Ala-His-Gly-Tyr-Ile-Arg (wherein, an amino acid residue is written by the 3 letters notation defined by IUPAC and IUB).

The homology search about each fragment with which the amino acid sequence was determined as mentioned above exhibited that the homology between these fragments and the known proteins was very low, except for exhibiting about 40% homology with hemolytic active proteins from *Carybdea rastonii*. Therefore, it was suggested that the specific protein of the present invention fractionated from the nematocyst of *Carybdea alata* while retaining the hemolytic activity is completely novel protein.

Example 4

Determination of the Full Amino Acid Sequence of the Protein and the Gene Encoding the Amino Acids 4-1) Preparation of total RNA of *Carybdea alata*

The tentacle (about 0.5 g in wet weights) of *Carybdea alata* was crushed in the liquid nitrogen, and homogenized in 5 ml TRIzol (registered trademark) reagent (GIBCO BRL Co.). To this mixture was added 1 ml of chloroform, and the mixture was agitated, and centrifuged with the cooling centrifuge (Sakuma Co.), 13,000 rpm, for 15 minutes, at 4° C. The upper aqueous layer was fractionated, and to this solution was added 2.5 ml of isopropanol, then, the mixture was allowed to stand at room temperature for 10 minutes. The supernatant fluid was removed after the centrifugal separation (13,000 rpm, for 10 minutes, at 4° C.) using the cooling centrifuge, and then 5 ml of 75% ethanol was added the residue. The supernatant fluid was removed after the centrifuge (10,000 rpm, for 5 minutes, at 4° C.) to obtain the residue, then, the air-drying of the residue was performed for about 10 minutes. 100 µl of RNase-free water was added to the resulting residue, and the mixture was incubated for 10 minutes at 60° C. to lyse RNA. About 0.5 mg of total RNA was obtained according to the above-mentioned method.

4-2) Cloning of a Partial cDNA

On the basis of amino acid sequence (1) and amino acid sequence (2), the following degenerate primers were designed and synthesized by the conventional method:

```
F-primer; GAY CAR GAR YTI GAR GAY AA

R-primer; ATR TAI CCR TGI GCI SWI SWY TCC
```

(wherein, the above-mentioned alphabetic character was written based on the "Nucleotide Abbreviation List" (Cell Technology, separate volume, "*Biotechnology Experiment Illustrated*". Shujunsha Co.).

Next, according to the following procedure, single-strand cDNA was synthesized using SUPERSCRIPT (registered trademark) Preamplification System for First Strand cDNA Synthesis. That is, 1 µg of total RNA, oligo(dT)$_{12-18}$(SEQ ID NO: 7), and DEPC-treated water were mixed, and the mixture was allowed to stand for 10 minutes at 70° C. Then, PCR buffer, 25 mM MgCl$_2$, 10 mM dNTP mix, and 0.1 M DTT were added to this mixture, and the resulting mixture was pre-incubated for 5 minutes at 42° C. Superscript II RT (200 units/µl) was added to this mixture, and the mixture was incubated for 50 minutes at 42° C. and for 15 minutes at 70° C. The RNase H was added to the mixture, and then, the resulting mixture was incubated for 20 minutes at 37° C. to obtain 1st-strand cDNA.

Subsequently, according to the following conditions, PCR was performed using GeneAmp PCR System 2400 thermal cycler (Perkin-Elmer Co.). That is, 1st-strand cDNA, PCR buffer, dNTP mix, F-primer, R-primer, TaKaRa Ex Taq (registered trademark, Takara Shuzo Co.), and water were mixed. The reaction was performed by heating the mixture at 94° C. for 5 minutes, then repeating 3 cycles of 30 seconds at 94° C., 30 seconds at 45° C. and 2 minutes at 72° C., and further 27 cycles of 30 seconds at 94° C., 30 seconds at 55° C. and 2 minutes at 72° C. The reactant was then treated for 5 minutes at 72° C.

The obtained reaction solution was electrophoresed on 0.8% agarose gel to confirm the amplified PCR product in the combination of F-primer and R-primer. The size of the PCR product was about 900 bp.

4-3) Sequencing of the Partial cDNA

The PCR product was inserted into TA cloning vector pCR2.1 (Invitrogen Co.), and the recombinant was transformed to the *Escherichia coli* JM109. The transformant was cultured on LB (containing 50 µg/µl of ampicillin) agar medium. According to the following conditions, colony PCR was performed to the colonies obtained as a template using the M13 universal primer. The strain of *Escherichia coli*, PCR buffer, dNTP mix, M13 FW primer, M13 RV primer, TaKaRa Ex Taq (registered trademark, Takara Shuzo Co.), and water were mixed. The reaction was performed by heating the mixture at 90° C. for 10 minutes, then repeating 30 cycles of 30 seconds at 94° C., 30 seconds at 55° C. and 2 minutes at 72° C., and further heating at 72° C. for 5 minutes. The reaction solution was electrophoresed on 0.8% agarose gel and the target colony PCR product was purified on the spin column of MicroSpin (registered trademark) S-400 (Amersham Pharmacia Co.). Then, the sequencing of the obtained product was conducted by using ABI PRISM 310 Genetic Analyzer (Applied Biosystems Co.).

The obtained sequence was analyzed using gene analysis soft ware GENETYX-MAC (Software Development Co.). As the result, the partial cDNA sequence of about 900 bp was analyzed.

4-4) Sequencing of the Full-length cDNA

Following primers were synthesized based on the base sequence of the partial cDNA:

```
5'-RACE-1R;    ACA GCA TCT CTG ACC GAA TC

5'-RACE-2R;    AAT GGA CCT CGG TCA GAT TC

5'-RACE-3R;    CAC TGT TGA CGA AGG TGA TG

3'-RACE-1F;    GGA ACA GCT GAT GAA GAT CC

3'-RACE-2F;    GGT GAG CAA GGT TAC TTC AC
```

Next, according to the following procedure, 5' RACE and 3' RACE were performed using 5'/3' RACE Kit (Boehringer Mannheim Co.).

(a) 5' RACE

1 µg of total RNA, cDNA synthesis buffer, dNTP mix, 5'-RACE-1R, AMV reverse transcriptase, and DEPC-treated water were mixed, and the mixture was incubated for 60 minutes at 55° C. and for 10 minutes at 65° C. to obtain 1st-strand cDNA.

Next, 1st-strand cDNA thus obtained was purified on the spin column, then, reaction buffer and 2 mM dATP were added to the 1st-strand cDNA, and the mixture was allowed to stand for 3 minutes at 94° C. Terminal transferase (10 units/µl) was added to the mixture, and the resulting mixture was incubated for 20 minutes at 37° C. After the incubation, 1st-strand cDNA, PCR buffer, dNTP mix, 5'-RACE-2R, oligo(dT)-anchor primer, and water were added to the above mixture. The reaction was performed by heating the mixture at 94° C. for 5 minutes, then repeating 30 cycles of 30 seconds at 94° C., 30 seconds at 55° C. and 1 minute at 72° C., and further heating at 72° C. for 5 minutes. Consequently, the nested-PCR was performed to the 1st-PCR product as a template using the combination of 5'-RACE-3R and PCR anchor primer under the same condition as 1st-PCR.

The 1st-PCR product and the nested-PCR product were electrophoresed on 1.5% agarose gel to confirm the band of about 600 bp. This nested-PCR product was inserted into TA cloning vector, and the sequencing was performed according to the determination of the base sequence of cDNA described in the above-mentioned 4-3), then the sequence was analyzed.

(b) 3' RACE

1 μg of total RNA, cDNA synthesis buffer, dNTP mix, oligo(dT)-anchor primer, AMV reverse transcriptase, and DEPC-treated water were mixed, and the mixture was incubated for 60 minutes at 55° C. Subsequently, the reactant was treated for 10 minutes at 65° C. to obtain 1st-strand cDNA.

Next, 1st-PCR thus obtained was performed under the following condition. 1st-strand cDNA, PCR buffer, dNTP mix, 3'-RACE-1F, PCR anchor primer, TaKaRa Ex Taq (registered trademark, Takara Shuzo Co.), and water were mixed. The reaction was performed by heating the mixture at 94° C. for 5 minutes, then repeating 30 cycles of 30 seconds at 94° C., 30 seconds at 55° C. and 2 minutes at 72° C., and further heating at 72° C. for 5 minutes. The nested-PCR was performed to the 1st-PCR product as a template using the combination of 3'-RACE-2F and PCR anchor primer under the same condition as 1st-PCR.

The 1st-PCR product and the nested-PCR product were electrophoresed on 1.5% agarose gel to confirm the band of about 600 bp. The nested-PCR product was inserted into TA cloning vector, the sequencing was performed according to the determination of the base sequence of cDNA described in the above-mentioned 4-3), and the sequence was analyzed.

As a result, the size (2000 bp) and the sequence of cDNA encoding the novel hemolytic active protein of *Carybdea alata*, and the number (463aa) and the sequence of amino acid of the protein became clear. That is, the hemolytic active protein of *Carybdea alata* has the amino acid sequence represented by SEQ ID NO 3, and the gene encoding thereof has the base sequence represented by SEQ ID NO 4.

The novel protein of the present invention obtained as mentioned above is the specific protein having the following physiological activity, and physical and chemical property, as indicated by the example:

(a) having hemolytic activity:
(b) having a molecular weight of about 50,000 Da (determined by SDS gel electrophoresis);
(c) having the amino acid sequences 1 and 2 described above as a partial amino acid sequence; and
(d) having the amino acid sequence represented by SEQ ID NO 3 as the full amino acid sequence.

INDUSTRIAL APPLICABILITY

Since the protein having the hemolytic activity derived from the nematocyst of *Carybdea alata* provided according to the present invention is a novel protein which is not similar to known protein, as a result of the homology search on the partial amino acid sequence and the full primary amino acid sequences, it is useful as a biochemical reagent for example, elucidating the mechanism of a hemolysis etc.

It also provides the new approach directed to development of drugs, such as the medicine for treating the sting by the jellyfish, on the basis of study of correlation of the structural activity in a molecular level, and the antibody on the protein or the partial peptide, etc. Furthermore, it is useful as the drugs having a platelet agglutination effect etc.; and pesticides using a hemolytic activity.

---

What is claimed is:

1. An isolated hemolytic protein, comprising the amino acid sequence of SEQ ID NO: 1 or SEQ ID NO: 2, wherein the hemolytic protein has a molecular weight of about 50,000 Da.

2. The hemolytic protein according to claim 1, wherein the protein is obtained from a nematocyst of *Carybdea alata*.

3. An isolated hemolytic protein, comprising a sequence selected from the group consisting of SEQ ID NO: 1, SEQ ID NO:2, wherein the protein is obtained from a cultivated product of a transformed cell prepared by genetic recombination.

4. An isolated hemolytic protein comprising the sequence of SEQ ID NO: 3.

5. The hemolytic protein according to claim 3, wherein the protein is obtained from the cultivated solution of a transformed cell prepared by genetic recombination using a polynucleotide which hybridizes with a polynucleotide encoding at least one amino acid sequence selected from the group consisting of SEQ ID NO: 1 and SEQ ID NO: 2.

6. A process for preparing the hemolytic protein of claim 1, comprising ultrasonicating at least one nematocyst of *Carybdea alata* in phosphoric acid buffer solution; centrifuging the mixture; extracting the supernatant fluid after centrifugation; and extracting the hemolytic protein from said supernatant by ion exchange high performance liquid chromatography or gel filtration high performance liquid chromatography.

7. The process for preparing the hemolytic protein of claim 6, wherein the phosphoric acid buffer solution is 10 mM phosphoric acid buffer solution of pH 6.0 containing at least 0.1 M NaCl at or below 10° C.

8. A pharmaceutical composition comprising the hemolytic protein according to claim 3.

9. The pharmaceutical composition to claim 8, wherein the composition has a platelet agglutination effect.

* * * * *